United States Patent [19]

Lorenz et al.

[11] 4,162,361

[45] Jul. 24, 1979

[54] MORPHINE/APOMORPHINE REARRANGEMENT PROCESS

[75] Inventors: Roman R. Lorenz; Edward D. Parady; William H. Thielking, all of Schodack, N.Y.

[73] Assignee: Sterling Drug Inc., New York, N.Y.

[21] Appl. No.: 907,901

[22] Filed: May 18, 1978

Related U.S. Application Data

[63] Continuation-in-part of Ser. No. 757,888, Jan. 10, 1977, abandoned.

[51] Int. Cl.² .................................................. C07D 215/14
[52] U.S. Cl. ................................................................ 546/72
[58] Field of Search ........................ 260/289 C; 546/72

[56] References Cited

PUBLICATIONS

Small et al., J. Org. Chem., 5, pp. 334–349, 1940.

Primary Examiner—Donald G. Daus
Assistant Examiner—D. B. Springer
Attorney, Agent, or Firm—William G. Webb; B. Woodrow Wyatt

[57] ABSTRACT

Apomorphine derivatives are prepared in improved yield by rearrangement of the corresponding morphine derivative in the presence of anhydrous orthophosphoric acid under a partial vacuum and hydrolysis of the resulting phosphate esters in an aqueous medium.

7 Claims, No Drawings

MORPHINE/APOMORPHINE REARRANGEMENT PROCESS

RELATED APPLICATIONS

This is a continuation-in-part of our prior, copending application Ser. No. 757,888 filed Jan. 10, 1977, now abandoned.

BACKGROUND OF THE INVENTION (a) Field of the Invention

This invention relates to an improved process for preparing apomorphine and its derivatives by rearrangement of the corresponding morphine derivative.

(b) Description of the Prior Art

The use of a variety of acids to effect the morphine/apomorphine type rearrangement by heating the corresponding morphine derivative with the acid is known, including concentrated aqueous zinc chloride solutions [Mayer, Ber. 4, 121-128 (1871)—apomorphine (no yield given); Matthiessen et al., Ann. 158, 131-135 (1871)—apocodeine (no yield given); German Pat. No. 489,185, Frdl. 16 (II), 2485-2486 (1927-1929)—apocodeine (25% yield) and apomorphine ethyl ether (2% yield)], concentrated hydrochloric acid [Matthiessen et al., Proc. Roy. Soc. (London) B17, 455-462 (1869)—apomorphine (no yield given)], anhydrous oxalic acid [Knorr et al., Ber. 40, 3355-3358 (1907)—apocodeine (no yield given); Folkers, J. Am. Chem. Soc. 58, 1814-1815 (1936)—apocodeine (12.8% yield); Corrodi et al., Helv. Chim. Acta. 38, 2038-2043 (1955)—norapocodeine (13% yield)], 85% or 90% phosphoric acid with current of anhydrous hydrogen chloride passed through mixture [Oparina, Khim. Farm. Prom. 15, 18-19 (1934); U.S.S.R. Pat. No. 40,981 (Jan. 31, 1935); C.A. 30, 7285 (1936)—apomorphine (40-42%); Hensiak, J. Med. Chem. 8, 557-559 (1965)—N-allylnorapomorphine (46% yield)], 85% phosphoric acid with current of nitrogen passed through mixture [Koch et al., J. Med. Chem. 11, 977-981 (1968)—apocodeine (20% yield), norapomorphine (13% yield), N-ethylnorapomorphine (36% yield), N-propylnorapomorphine (37% yield), N-propargylnorapomorphine (20% yield), N-cyclopropylmethylnorapomorphine (33% yield), N-benzylnorapomorphine (37% yield), N-phenethylnorapomorphine (16% yield)], aqueous glacial phosphoric acid [$(HPO_3)_n$-See Merck Index-Eighth Edition, page 824] [Wright, J. Chem. Soc. 25, 652-657 (1872)—apomorphine (0.6% yield)] and glacial phosphoric acid [Small et al., J. Org. Chem. 5, 334-349 (1940)—apocodeine (30% yield)].

SUMMARY

This invention relates in a process aspect to a process for preparing apomorphine or N-($R_2$)-norapomorphines, where $R_2$ has a significance to be described hereinafter, comprising reacting morphine or an N-($R_2$)-normorphine with anhydrous orthophosphoric acid under a partial vacuum and hydrolyzing the resulting phosphate esters in an aqueous medium.

DETAILED DESCRIPTION INCLUSIVE OF THE PREFERRED EMBODIMENT

As indicated above, the morphine/apomorphine rearrangement has previously been carried out on a wide variety of morphine derivatives using a variety of acid catalysts. However the yield obtained in all procedures described in the prior art is usually very poor, ranging from 0.6% to 46% depending upon the particular acid catalyst and morphine derivative used in the rearrangement, the yield in most cases being around 20-30%.

Apomorphines are very valuable compounds for use in medicine as emetics, hypotensive agents and CNS stimulants (Archer, U.S. Pat. No. 3,717,643 patented Feb. 20, 1973) or in the treatment of Parkinsonism (German Application No. 2,154,162, published May 3, 1973). While apomorphines have been successfully synthesized in the laboratory [see for example Späth and Hromatka, Ber. 62, 325 (1929); Avenarius and Pschorr, Ber. 62, 321 (1929), whose claim to a total synthesis has however been challenged by Gulland, Chem. and Ind. 16, 774 (1938); Neumeyer et al., J. Med. Chem. 16, 1223 (1973) and Neumeyer et al., J. Med. Chem. 16, 1228 (1973)], none of the methods so far devised are commercially feasible, since they all involve multiple synthetic steps and furthermore require resolution of optical isomers at some stage in the synthesis. The classical morphine/apomorphine rearrangement thus remains the most practical source of apomorphines, since derivatives of naturally occurring morphine or its relatives (e.g. heroin or codeine) are readily available, can be conveniently derivatized by simple chemical transformations either prior or subsequent to rearrangement, and during rearrangement maintain the natural steric configuration of the only original asymmetric center which is not destroyed by the rearrangement. The only drawback to more widespread commercial use of the rearrangement is the poor yield normally obtained in the reaction. In view of the pharmacological importance of apomorphines, there is thus a great need to improve the yield obtained in the morphine/apomorphine rearrangement.

It has now been surprisingly found that apomorphines, such as apomorphine itself or apocodeine, or norapomorphine derivatives, can be prepared in vastly improved yield over what was previously available using prior art processes by heating a corresponding morphine or normorphine derivative with anhydrous orthophosphoric acid ($H_3PO_4$) under a partial vacuum and hydrolyzing the resulting phosphate esters in an aqueous medium.

A preferred group of apomorphines and $R_2$-norapomorphines prepared by the present process are those having the formula I:

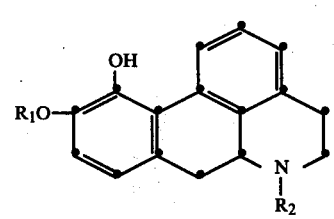

I where $R_1$ is hydrogen or lower-alkyl; and $R_2$ is hydrogen, lower-alkyl, lower-alkenyl, lower-alkynyl, phenyl-lower-alkyl or cycloalkyl-lower-alkyl which are prepared by rearrangement of morphine derivatives of the formula II:

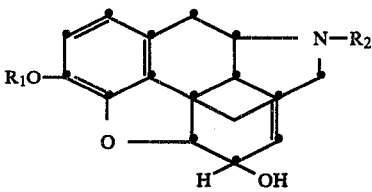

where $R_1$ and $R_2$ have the meanings given above. A particularly preferred group of apomorphines and $R_2$-norapomorphines prepared by the present process are those of formula I where $R_1$ is hydrogen or lower-alkyl; and $R_2$ is lower-alkyl or phenyl-lower-alkyl.

The process of the invention is carried out by heating the compounds of formula II in anhydrous orthophosphoric acid ($H_3PO_4$) at a temperature in the range from about 125° to 140° C. under a partial vacuum and hydrolyzing the resulting phosphate esters in an aqueous medium. While the practical lower limit to the operable pressure that can be used cannot be precisely defined, the pressure and temperature obviously should be such that the phosphoric acid is not evaporated off during the course of the reaction. In practice it has been found that a vacuum obtained from a water aspirator vacuum pump (i.e. about 9 to 20 mm.) is entirely suitable. In some instances, the reaction mixture tends to froth in the early minutes of the reaction, and such frothing is best controlled by increasing the pressure slightly until the frothing subsides. Thus it may be necessary to use pressures up to about 50 to 60 mm. in the early minutes of the reaction.

The rearrangement is usually completed in about 12-25 minutes, and it is advantageous to terminate the reaction and work up the product as soon as the rearrangement is complete. The work-up procedure involves first hydrolyzing the reaction product, consisting chiefly of phosphate esters of the apomorphine product, in an aqueous medium and isolating the product from the hydrolysis mixture. Hydrolysis can be carried out at ambient temperature, but it is advantageous to warm the mixture in order to expedite the hydrolysis reaction.

The course of the reaction is readily followed by thin layer chromatography, and since the products of the reaction are all known, they can be identified, for example, by comparison of their melting points with the known melting point values for the compounds or by mixed melting point determinations.

As used herein the term lower-alkyl means a saturated hydrocarbon group, which may be straight or branched, containing from one to five carbon atoms. The term thus includes, but is not limited to, methyl, ethyl, propyl, isopropyl, butyl and amyl.

The term lower-alkenyl means an unsaturated radical having one double bond, which may be straight or branched, and containing from three to five carbon atoms. The term thus includes, but is not limited to, 1-(2-propenyl), 1-(2-methyl-2-propenyl), 1-(3-methyl-2-butenyl) or 1-(2-butenyl).

The term lower-alkynyl means an unsaturated radical having one triple bond, which may be straight or branched, and containing from three to five carbon atoms. The term thus includes, but is not limited to, 1-(2-propynyl), 1-(2-methyl-2-propynyl), 1-(3-methyl-2-butynyl) or 1-(2-butynyl).

The term cycloalkyl means a saturated carbocyclic group containing from three to six ring carbon atoms as illustrated, for example, by cyclopropyl, cyclobutyl, cyclopentyl, cyclohexyl, 2-methylcyclobutyl or 4-ethylcyclohexyl.

SPECIFIC EXEMPLARY DISCLOSURE

The process of the present invention is illustrated by the following description.

A series of morphine/apomorphine rearrangements was carried out under five sets of process conditions designed to compare the yields obtained under the conditions of the present invention (Condition D) either as compared with conditions used in the prior art (Condition A—Koch et al.) or under conditions designed to determine the effect of other single reaction parameters such as the nature of the acid used (Condition B) or combinations of reaction parameters such as the use of nitrogen, a vacuum or anhydrous vs. 85% phosphoric acid (Conditions C and E). These reaction conditions are as follows:

Condition A—The starting material was heated with 85% orthophosphoric acid while passing a stream of nitrogen through the mixture.

Condition B—The starting material was heated with 85% orthophosphoric acid under water aspirator vacuum.

Condition C—The 85% orthophosphoric acid was flushed with nitrogen while heating, and rearrangement was then carried out with heating under application of a water aspirator vacuum.

Condition D—The starting material was heated with anhydrous orthophosphoric acid under a water aspirator vacuum.

Condition E—The starting material was heated with anhydrous orthophosphoric acid while passing a stream of nitrogen through the mixture.

In each case the starting material was added to the phosphoric acid after the latter had been heated to 70° C. When reaction was complete in each case (as indicated by thin layer chromatographic analysis on small samples which were warmed with water to hydrolyze the phosphate esters formed and extraction of the organic product into chloroform), each reaction mixture was worked up according to a standard procedure which is described as follows: The reaction mixture was poured into 600 ml. of ice water and allowed to stand overnight. The mixture was then heated to boiling for fifteen minutes, then cooled and poured slowly into 650 ml. of saturated brine. The aqueous layer was decanted from the gum which formed, and the gum was dissolved in 400 ml. of water and made basic by the addition of sodium sulfite. The mixture was then extracted with isopropyl acetate, the organic solution filtered, dried over anhydrous calcium sulfate and then acidified with ethereal hydrogen chloride. The hydrochloride salt which thus formed was collected, recrystallized from an appropriate solvent, identified by its melting point and weighed. The results obtained, expressed in terms of percent yield, are given in the following tables where the reaction condition used, i.e. Conditions "A", "B", "C", "D", or "E", and the maximum temperature and the total time of heating are given.

Results obtained in a series of runs for the rearrangement of N-propylnormorphine to N-propylnorapomorphine are given in the following table. The product in each case was recrystallized from n-butanol.

| Run | Cond. | Max.T(°C.)/Time (min.) | % Yield |
|---|---|---|---|
| 1 | A | 142/41 | 49.0 |
| 2 | A | 142/38 | 50.8 |
| 3 | A | 145/75 | 39.2 |
| 4 | A | 142/44 | 21.7 |
| 5 | A | 142/45 | 33.0 |
| 6 | A | 143/55 | 30.1 |
| 7 | A | 148/50 | 33.9 |
| 8 | A | 145/50 | 13.2 |
| 9 | A | 145/40 | 33.9 |
| 10-1 | A | 146/43 | |
| 10-2 | A | 145/40 | (a) 9.4 |
| 11 | A | N.A. | (b) 15.4 |
| 12 | A | 145/20 | 24.1 |
| 13 | A | 145/25 | 16.3 |
| 14 | A | 140/18 | 23.6 |
| | | AVERAGE YIELD | 28.1 |
| 1 | B | 140/25 | 32.1 |
| 2 | B | 130/13 | 28.3 |
| | | AVERAGE YIELD | 30.2 |
| 1 | C | 130/10 | 41.6 |
| 2 | C | 130/13 | 42.5 |
| | | AVERAGE YIELD | 42.1 |
| 1 | D | 130/15 | 53.5 |
| 2 | D | 128/13 | 40.6 |
| 3 | D | 132/13 | 46.8 |
| 4 | D | 132/17 | 43.6 |
| 5 | D | 134/15 | 50.1 |
| 6 | D | 130/15 | 39.3 |
| 7 | D | 130/15 | 48.6 |
| 8 | D | 128/16 | 49.1 |
| 9 | D | 130/15 | 58.6 |
| 10 | D | 130/15 | 51.1 |
| | | AVERAGE YIELD | (c) 48.1 |
| 1 | E | 150/25 | 22.6 |
| 2 | E | 150/25 | 21.8 |
| | | AVERAGE YIELD | 22.2 |

(a) Two runs. Yield based on combined products.
(b) Not available.
(c) Does not include two runs in which products were worked up in a totally different manner than the standard procedure and atypical yields, 30.2% and 23.6% respectively obtained.

Results obtained for the rearrangement of codeine to apocodeine are given in the following table. The product in each case was recrystallized from water.

| Run | Cond. | Max.T(°C.)/Time(min.) | % Yield |
|---|---|---|---|
| 1 | A | 145/45 | 19.7 |
| 2 | A | 145/45 | 17.2 |
| 3 | A | 140/40 | 18.3 |
| | | AVERAGE YIELD | 18.4 |
| 1 | D | 140/20 | 59.2 |
| 2 | D | 140/25 | 70.5 |
| | | AVERAGE YIELD | 64.9 |

Results obtained in the rearrangement of morphine to apomorphine are given in the following table. The products in each case were recrystallized from isopropyl acetate/diethyl ether.

| Run | Cond. | Max.T(°C.)/Time(min.) | % Yield |
|---|---|---|---|
| 1 | A | 140/45 | 10.0 |
| 2 | A | 140/45 | 14.0 |
| | | AVERAGE YIELD | 12.0 |
| 1 | D | 130/14 | 58.4 |
| 2 | D | 130/15 | 54.6 |
| | | AVERAGE YIELD | 56.5 |

Results obtained for the rearrangement of N-phenethylnormorphine to N-phenethylnorapomorphine are given in the following table. The products in each case were recrystallized from isopropyl acetate/diethyl ether.

| Run | Cond. | Max.T(°C.)/Time(min.) | % Yield |
|---|---|---|---|
| 1 | A | 138/45 | 25.4 |
| 2 | A | 138/45 | 22.9 |
| | | AVERAGE YIELD | 24.2 |
| 1 | D | 130/15 | 64.0 |
| 2 | D | 130/15 | 68.0 |
| | | AVERAGE YIELD | 66.0 |
| 1 | E | 150/40 | 53.0 |
| 2 | E | N.A. | 61.0 |
| 3-1 | E (a) | 150/25 | |
| 3-2 | E | 150/25 | 35.6 |
| | | AVERAGE YIELD | 49.9 |

These results show that, under the conditions of the instant process, i.e. reaction Condition D, the yield obtained in the morphine/apomorphine rearrangement for a variety of morphine derivatives is in the range from about 48–66%. In contrast the conditions used in the prior art (i.e. Condition A—Koch et al.) afford yields in the range from 12–28%.

We claim:

1. The process for preparing a compound having the formula:

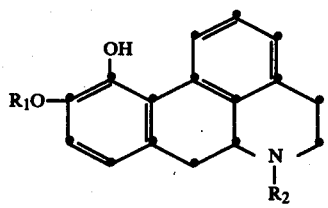

where $R_1$ is hydrogen or lower-alkyl; and $R_2$ is hydrogen, lower-alkyl, lower-alkenyl, lower-alkynyl, phenyl-lower-alkyl or cycloalkyl-lower-alkyl which comprises the steps of heating at a temperature in the range from 125° to 140° C. a compound having the formula:

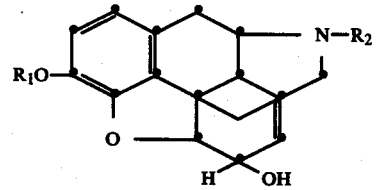

where $R_1$ and $R_2$ have the meanings given above with anhydrous orthophosphoric acid under a partial vacuum and hydrolyzing the resulting phosphate esters in an aqueous medium.

2. The process according to claim 1 for preparing a compound having the formula:

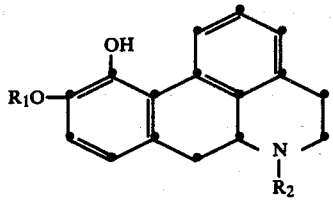

where $R_1$ is hydrogen or lower-alkyl; and $R_2$ is lower-alkyl or phenyl-lower-alkyl which comprises the steps of heating a compound having the formula:

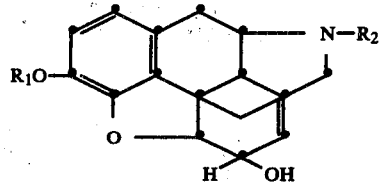

where $R_1$ and $R_2$ have the meanings given above with anhydrous orthophosphoric acid under a partial vacuum and hydrolyzing the resulting phosphate esters in an aqueous medium.

3. The process according to claim 2 where the reaction is carried out at a pressure of 9 to 20 mm.

4. The process according to claim 2 for preparing N-propylnorapomorphine from N-propylnormorphine.

5. The process according to claim 2 for preparing apocodeine from codeine.

6. The process according to claim 2 for preparing apomorphine from morphine.

7. The process according to claim 2 for preparing N-phenethylnorapomorphine from N-phenethylnormorphine.

* * * * *